United States Patent [19]

Yang et al.

[11] Patent Number: 5,041,595

[45] Date of Patent: Aug. 20, 1991

[54] METHOD FOR MANUFACTURING VINYLALKOXYSILANES

[75] Inventors: Wei-Tai Yang; James S. Ritscher, both of Marietta, Ohio

[73] Assignee: Union Carbide Chemicals and Plastics Technology Corporation, Danbury, Conn.

[21] Appl. No.: 588,161

[22] Filed: Sep. 26, 1990

[51] Int. Cl.$^5$ ................................................ C07F 7/18
[52] U.S. Cl. ..................................................... 556/479
[58] Field of Search ......................................... 556/479

[56] References Cited

U.S. PATENT DOCUMENTS

| | | | |
|---|---|---|---|
| 2,637,738 | 5/1952 | Wagner | 260/448.2 |
| 2,823,218 | 2/1958 | Speier et al. | |
| 3,153,662 | 10/1964 | Pike | 556/479 |
| 3,404,169 | 10/1968 | Gaignon et al. | 556/479 |
| 3,666,782 | 5/1972 | Mui et al. | |
| 3,793,358 | 2/1974 | Bauer et al. | |
| 4,089,882 | 5/1978 | Takamizawa et al. | 556/479 |
| 4,254,271 | 3/1981 | Fuike et al. | 556/479 |
| 4,579,965 | 4/1986 | Kanner et al. | |
| 4,668,812 | 5/1987 | Quirk et al. | |
| 4,727,173 | 2/1988 | Mendicino | |
| 4,730,074 | 3/1988 | Lewis et al. | |
| 4,898,961 | 2/1990 | Baile et al. | 556/479 |

FOREIGN PATENT DOCUMENTS

| | | | |
|---|---|---|---|
| 57-4995 | 1/1982 | Japan | |
| 64-83089 | 3/1989 | Japan | 556/479 |
| 1380306 | 1/1975 | United Kingdom | |

OTHER PUBLICATIONS

Chemical Abstracts, 78(11):72359g (1973).
Chemical Abstracts, 79(25):146646t (1973).
Chemical Abstracts, 80(23):133541a (1974).
Chemical Abstracts, 86(19):140237h (1977).
Chemical Abstracts, 93(23):220827k (1980), *J. Organometallic Chem.*, 195(3):363-73 (1980).

*Primary Examiner*—Paul F. Shaver
*Attorney, Agent, or Firm*—Bonnie L. Deppenbrock

[57] ABSTRACT

A process for directly producing a high purity vinylalkoxysilane by gradually feeding an alkoxysilane containing low levels of ionic chloride or alkyl amine into a reaction zone containing an alkyne and a platinum hydrosilation catalyst.

24 Claims, No Drawings

METHOD FOR MANUFACTURING VINYLALKOXYSILANES

BACKGROUND OF THE INVENTION

1. Field of the Invention

This invention relates to a method for producing vinylalkoxysilanes at high purity. In particular, the present invention is directed to an efficient method for producing vinylalkoxysilanes by direct hydrosilation of an alkyne with alkoxysilane.

2. Description of Related Art

Vinyl silyl esters, also known as vinyl silyl ethers, hereinafter referred to as vinylalkoxysilanes, are commercially important compositions of matter. These materials are used as coupling agents in thermoplastic composites, in fiberglass primers, and in cable insulators. Vinylalkoxysilanes also are used as co-monomers in water-curable (cross-linkable) polyolefin-containing plastics. In this latter application, in particular, it is important that a high source of the vinylalkoxysilane be available, the presence of even small amounts of such impurities as tetraalkoxysilanes and alkylalkoxysilanes in the vinylalkoxysilane is unwanted. These impurities are particularly troublesome because the closeness of their boiling points to that of the desired vinylalkoxysilane makes their removal therefrom via distillation practically impossible.

Diverse methods of manufacturing vinylalkoxysilanes and related compounds are known, but none has been completely satisfactory for producing a high purity product. In one approach, a vinylchlorosilane is esterified with an alcohol in accordance with the following reaction:

$$RCH=CHSiCl_3 + 3R'OH \rightarrow RCH=CHSi(OR')_3 + 3HCl \qquad 1a$$

wherein R is an alkyl group or hydrogen, and R' generally is an alkyl or an aryl group. Removal of by-product hydrogen chloride is time consuming and by its nature only partially successful, thus imposing practical purity limits on the product. Furthermore, side reactions encountered during the preparation of the vinylchlorosilane degrades the actual yield of vinylalkoxysilane from the alkyne.

The vinylchlorosilane initially is prepared by hydrosilation of an alkyne with a trichlorosilane, as follows:

$$RC\equiv CH + HSiCl_3 \rightarrow RCH=CHSiCl_3 \qquad 1b$$

with R as defined above. Unfortunately, the following side reaction also takes place and reduces the theoretical yield of the desired vinylalkoxysilane from the alkyne:

$$RCH=CHSiCl_3 + HSiCl_3 \rightarrow Cl_3SiCHRCH_2SiCl_3 \qquad 1c$$

In an alternative approach, the vinylalkoxysilane can be prepared by first reacting an alkene with an aminosilane in the presence of a catalyst according to the following reaction:

$$RCH=CH_2 + HSi(NMe_2)_3 \longrightarrow \qquad 2a$$

-continued
$$RCH=CHSi(NMe_2)_3(87\%) + RCH_2CH_2Si(NMe_2)_3(11\%) + H_2$$

The vinylaminosilane thus produced then is alkoxylated with an alcohol according to the following reaction:

$$RCH=CHSi(NMe_2)_3 + 3R'OH \rightarrow RCH=CHSi(OR')_3 + 3HNMe_2 \qquad 2b$$

As with the prior method, side reactions and the presence of by-products, particularly dimethylamine, reduce the theoretical yield and purity of the desired vinylalkoxysilane product.

The prior art also has disclosed the direct hydrosilation of an alkyne using an alkoxysilane over a variety of catalysts, in accordance with the following formula:

$$RC\equiv CH + HSi(OR')_3 \rightarrow RCH=CHSi(OR')_3 \qquad 3a$$

This approach is potentially superior to the previously described routes because of its simplicity as a one-step reaction and because formation of the desired vinylalkoxysilane, in theory, is not necessarily accompanied by the formation of certain by-products such as dimethylamine or hydrogen chloride.

U.S. Pat. No. 2,637,738 describes the reaction of triethoxysilane with acetylene in the presence of a catalyst comprising platinum supported on finely divided charcoal to form vinyltrialkoxysilane. The reaction was conducted at a temperature of about 130° C. and at a gas pressure of from about 2 atmospheres (Table III), where no vinylsilane was formed, up to about 20 atmospheres (Example 2), where the vinylsilane was the major product, by charging acetylene to an agitated reactor containing the triethoxysilane and the platinum catalyst. Unfortunately, the reported yield of the desired vinyltrialkoxysilane is rather low, being accompanied in all reported cases by a substantial quantity of by-product bis(alkoxysilyl)alkane, i.e., 1,2-bis(triethoxysilyl)ethane, produced as a consequence of the following reaction:

$$RCH=CHSi(OR')_3 + HSi(OR')_3 \rightarrow (R'O)_3SiC(R)HCH_2Si(OR')_3 \qquad 3b$$

Still other by-products include the related alkylalkoxysilanes and the tetraalkoxysilane whose formation by the following reactions normally is favored by elevated reaction temperatures:

$$2HSi(OR)_3 \rightarrow Si(OR)_4 + H_2Si(OR)_2 \qquad 3c$$

$$CH_2=CHSi(OR)_3 + H_2 \rightarrow CH_3CH_2Si(OR)_3 \qquad 3d$$

$$CH\equiv CH + H_2 + HSi(OR)_3 \rightarrow CH_3CH_2Si(OR)_3 \qquad 3e$$

Hydrogen for these reactions can be formed during the preparation of the desired product by dehydrogenation of the platinum/vinyl complex which is formed during the reaction sequence in which the bis(alkoxysilyl)alkane compound is formed. Hydrogen also may possibly be formed by the following condensation reaction:

$$2HSi(OR)_3 \rightarrow (RO)_3SiSi(OR)_3 + H_2 \qquad 3f$$

A method disclosed in U.S. Pat. No. 2,823,218 utilizes chloroplatinic acid ($H_2PtCl_6.6H_2O$) to catalyze reactions involving a silicon-hydrogen bond and an unsaturated carbon-carbon bond. The method is said to increase the yield of the desired product, decrease the yield of by-products, and lower the necessary reaction temperature. Example 21 describes adding acetylene to a reactor containing triethoxysilane and an isopropanol solution of chloroplatinic acid to produce vinyltrialkoxysilane. Yield and purity information is not reported.

Japanese Kokai 57/4995 (1982), in Comparison Example 13, discloses adding acetylene to a reactor containing 80 mmol of trimethoxysilane and chloroplatinic acid catalyst solution dissolved in 70 ml of xylene as a solvent. The hydrosilation reaction was conducted at a reaction temperature of 60° C. and at normal pressure. A major product formed was 1,2-bis(trialkoxysilyl)ethane.

Reaction of a tri-t-alkoxysilane with an alkyne in the presence of a platinum hydrosilation catalyst at a temperature greater than about 150° C. to produce a vinyl-tri-t-alkoxysilane is disclosed in U.S. Pat. No. 4,579,965. The patent discloses that production of undesired bis(-tri-t-alkoxysilyl)ethane is very low. Suggested platinum hydrosilation catalysts include platinum metal (alone or on a support), chloroplatinic acid, and platinum(II) 2,4-pentanedionate.

Notably, this patent discloses that when a primary or secondary alkoxysilane (e.g., trimethoxysilane, triethoxysilane, or triisopropoxysilane), instead of the tertiary alkoxysilane, is reacted with acetylene, formation of the undesired bis(silylalkoxy)alkane derivative predominates over the desired reaction yielding the vinylalkoxysilane. In particular, Comparative Examples 2 through 4 show that the bis-silyl derivative predominates when acetylene is added to a mixture of a primary or secondary trialkoxysilane and a chloroplatinic acid catalyst. Although relative selectivity improved when $PtCl_2(PPh_3)_2$ was utilized in place of chloroplatinic acid catalyst, desired product yield remained at only 80 percent for primary alkoxysilanes. Furthermore, in each such case, the yield of tetraalkoxysilane and alkylalkoxysilanes by-products was at least 2 wt. percent. As noted above, these unwanted by-products are exceedingly difficult to remove from the desired vinylsilane product.

Some approaches for increasing the yield of the desired vinylsilane produced via direct hydrosilation of an alkyne using a trialkoxysilane are not commercially practicable. One possible expedient involves significantly increasing the pressure of the alkyne, ($RC\equiv CH$), such as acetylene, to as high as 20 atmospheres. Unfortunately, an acetylene pressure higher than about 1 to 4 atmospheres (gauge) creates a significant safety hazard.

U.S. Pat. No. 3,793,358 discloses a method for manufacturing alkenylhaloalkylsilanes (vinylhaloalkylsilanes) from a halosilane and an alkyne. Hydrosilation of an alkyne with a trialkoxysilane is not disclosed or suggested. In accordance with the disclosed method, a mixture of the alkyne and a silane having one or two silicon-hydrogen bonds, with the remaining silicon valence bonds occupied by a halogen or an inert monovalent organic radical, such as an alkyl, aryl, or cycloalkyl radical, is added to a reactor containing an addition catalyst and a disilylethane (bis-silylethane) solvent or diluent. The disilylethane used is preferably the same one which is formed as a by-product of the hydrosilation reaction. A reaction temperature between 120° and 220° C. and a reaction pressure between 0.1 and 5.0 atmospheres are utilized. Suitable addition catalysts include chloroplatinic acid and preferably its reaction products and complexes. This patent does not describe how to minimize or avoid the formation of inseparable by-products, such as the alkylsilanes, when producing vinylalkoxysilanes.

The prior art has failed to define a direct process for producing high-purity vinylalkoxysilanes in high yield from an alkoxysilane.

DESCRIPTION OF THE INVENTION

The subject invention relates to an efficient and direct, i.e., one-step, method for producing high purity vinylalkoxysilanes by hydrosilating an alkyne. In accordance with the present method, an alkyne of the formula $RC\equiv CH$, where R is hydrogen or a monovalent hydrocarbon radical of 1 to 10 carbon atoms, is hydrosilated with an alkoxysilane of the formula $HSi(OR')_nR''_{3-n}$ where R' and R'', which individually can be the same or different, are selected from primary alkyl groups of 1 to 6 carbon atoms, preferably 1 to 4 carbon atoms, and n is 1, 2, or 3.

The hydrosilation reaction is carried out in the presence of a platinum hydrosilation catalyst, preferably chloroplatinic acid, and in a reaction medium containing low levels of ionic chloride and alkyl amine contaminants. Applicants have found that by limiting the level of such contaminants, the production of hard to remove by-products during hydrosilation is minimized.

The reaction is conducted by gradually feeding the alkoxysilane to a reaction zone containing the alkyne. The reaction zone is operated at a low temperature (generally less than about 150° C.) and optionally, although preferably, at a low pressure (generally less than about 75 psia).

The reaction can be run either continuously or in a batchwise manner. Based on economical considerations, continuous operation generally is preferred, although in certain circumstances other considerations, including issues of safety and convenience, may favor batchwise operation. When operating in a continuous manner, the acetylene and alkoxysilane reactants are fed into the reaction zone simultaneously with the removal of hydrosilation products.

In a preferred embodiment of the present invention, acetylene from the gas phase is reacted with an alkoxysilane in the liquid phase in the presence of a hydrosilation catalyst to yield a vinylalkoxysilane. Consequently, good mixing is important in the process of the present invention; since it generally serves as the primary mechanism driving acetylene from the gas phase into the liquid phase where the hydrosilation reaction takes place. The liquid reaction phase is referred to herein in the alternative as the reaction medium. As a general rule, the vinylalkoxysilane product purity is improved as the degree of mixing is increased until conditions approaching a completely mixed system are reached. A suitable level of mixing for any reactor design can be determined using routine experimentation.

An important feature of the present invention is that conditions in the reaction zone must be controlled so that the alkyne, e.g., acetylene, is present in the reaction medium, for the most part, in an amount of at least about its stoichiometric equivalent relative to the concentration of the alkoxysilane. Preferably, the alkyne is present in the reaction medium in a stoichiometric excess, relative to the concentration of alkoxysilane in the reaction medium. While it may not be possible to measure precisely the concentrations of the alkyne and alkoxysilane in the reaction medium, so as to assess quantitatively the molar ratio in the reaction medium, one skilled in the art can be confident of establishing and maintaining the above-stated condition of at least a molar equivalent and preferably a molar excess of the alkyne by operating in accordance with the method of the present invention as more fully described below.

Thus, in accordance with the method of the present invention, the alkoxysilane reactant is fed gradually into a hydrosilation reaction zone, containing a stoichiometric excess of an alkyne (acetylene) and is contacted in said reaction zone with said alkyne in the presence of a platinum hydrosilation catalyst. Preferably, the alkoxysilane is fed into the reaction zone at a rate substantially equivalent to the rate at which it is consumed therein by reaction with the alkyne, so that alkoxysilane does not accumulate in the reaction zone during the hydrosilation reaction. The alkoxysilane reactant preferably should not be present in the reaction zone in a molar excess relative to the alkyne (acetylene).

In a preferred embodiment, wherein the hydrosilation reaction is conducted in a continuous fashion, acetylene and the alkoxysilane are co-fed into a reaction zone containing said acetylene and a platinum hydrosilation catalyst. By prior introduction of at least a part of the alkyne, i.e., acetylene into the reactor, which in the case of acetylene establishes an atmosphere of acetylene in the reaction zone, preferably at a superatmospheric pressure, it is possible to maintain in the reaction medium under conditions of good mixing, for the most part, an instantaneous molar ratio of alkyne to alkoxysilane of greater than about 1.0 and more preferably greater than about 2.0. The hydrosilation reaction then is initiated by feeding the alkoxysilane gradually into the reaction zone and contacting it with the alkyne in the presence of the hydrosilation catalyst.

Preferably the reactants are co-fed substantially at the rate they are consumed by the hydrosilation reaction in the reaction zone. In the case of acetylene, this rate of feeding can readily be maintained simply by introducing acetylene into the reaction zone on demand to maintain a desired gas phase pressure in the reaction zone. As regards the alkoxysilane, applicants have found that a feed rate in the range of about 2.0 to about 8.0 g-mole/hr.-liter of reaction medium, should be suitable in most circumstances. It is preferred to maintain the alkyne (acetylene) reactant concentration in the reaction zone at a molar ratio of about 1.0 to about 10.0, and more usually between about 2.0 and about 5.0, times the molar concentration of the alkoxysilane in the reaction zone. In combination with good mixing, demand feeding of the alkyne, particularly acetylene, under these conditions insures that a proper amount of acetylene is delivered into the reaction zone and then into the reaction medium to maintain the desired stoichiometric balance of the alkyne and alkoxysilane.

As used throughout the specification and claims, gradual addition of the alkoxysilane to the reaction zone means that the instantaneous rate of addition of the alkoxysilane to the reaction zone is preferably not more than about 4.0 times and more preferably not more than about 2.0 times the rate at which alkoxysilane is consumed in the reaction medium. In other words, it is possible to add the alkoxysilane to the reaction zone in segmented portions or stages, rather than adding it continuously at a substantially constant rate. This latter operation, one embodiment of which is often referred to in the art as pulse feeding, is generally not preferred, since it tends to result in higher amounts of the bis(alkoxysilyl)alkane being formed as compared with continuous feeding of the alkoxysilane at a substantially constant rate. Nonetheless, this operation is superior to the prior art batchwise approach for preparing vinylalkoxysilanes where the total alkoxysilane charge is added to the reactor prior to the start of the reaction.

As described above, in accordance with the method of the present invention, an alkyne is hydrosilated with an alkoxysilane. As the alkyne it is possible to use, in the process according to the present invention, acetylene per se or a substituted acetylene which has been used previously for the manufacture of alkenylsilanes by addition of alkynes to silicon compounds with an Si-bonded hydrogen. Thus, alkynes suitable for use in the present invention are especially compounds of the general formula $RC\equiv CH$, wherein R is hydrogen or a monovalent hydrocarbon radical having 1 to 10 carbon atoms such as an alkyl, a cycloalkyl or an aryl. Preferably, R is hydrogen or a monovalent hydrocarbon radical having 1 to 6 carbon atoms. More preferably, R is selected from the group consisting of hydrogen, phenyl, and methyl. Most preferably, R is hydrogen, i.e., the alkyne is acetylene.

Suitable substituted acetylenes include phenylacetylene, propyne, 1-butyne, and 1-pentyne. However, since acetylene is more easily accessible than substituted acetylenes and since silanes with unsubstituted vinyl groups are of special commercial importance, the use of acetylene ($HC\equiv CH$) is preferred in the process according to the present invention. If desired, it is also possible to employ mixtures of acetylene and one or more substituted acetylenes or mixtures of different substituted acetylenes in the process according to the present invention. The optionally substituted acetylene is advantageously employed in the anhydrous form.

Suitable alkoxysilanes for practicing the present invention are selected from the group consisting of trialkoxysilanes, alkyldialkoxysilanes, and dialkylalkoxysilanes of the formula $HSi(OR')_nR''_{3-n}$ where $R'$ and $R''$, which individually can be the same or different, are selected from primary alkyl groups of 1 to 6 carbon atoms, preferably 1 to 4 carbon atoms, and n is 1, 2, or 3. As exemplary alkoxysilanes can be mentioned trimethoxysilane, triethoxysilane, tris(methoxyethoxy)silane, tributoxysilane, methyldimethoxysilane, dimethylmethoxysilane, methyldiethoxysilane, tripropoxysilane, tripentoxysilane, and tris(2-ethylhexoxy)silane. Trialkoxysilanes and alkyldialkoxysilanes are preferred, particularly those where the alkyl groups have one or two carbon atoms. Most preferably, trimethoxysilane and triethoxysilane are utilized as the alkoxysilane.

As hydrosilation catalysts it is possible to use, in the process according to the present invention, those platinum catalysts that have previously been employed as catalysts in the manufacture of alkenylsilanes by addition of optionally substituted acetylene to silicon compounds with a Si-bonded hydrogen, provided that the particular catalysts are sufficiently stable under the reaction temperatures chosen. Examples of substances which can be used as hydrosilation catalysts in the process according to the present invention are especially soluble platinum compounds such as chloroplatinic acid ($H_2PtCl_6 6H_2O$), platinum organic complexes, such as platinum-phosphine complexes (including for example $PtX_2(PPh_3)_2$ and the like), and platinum(II) bis 2,4-pentanedionate, and platinum metal optionally on a solid support, such as carbon black, silica gel, calcium carbonate, and the like. Chloroplatinic acid, its solutions and reaction products or complexes of chloroplatinic acid with other inorganic and/or organic compounds are preferred. Normally, the chloroplatinic acid is added to the reaction zone as a solution in an inert, organic solvent such as an alcohol, ketone or ether. The solvent in which the chloroplatinic acid is dissolved conveniently can be the same solvent utilized as solvent or diluent for the reactants.

Catalyst is employed in a quantity sufficient to catalyze the hydrosilation reaction. The expense of a platinum-containing catalyst typically makes it desirable to minimize to the extent possible the quantity of catalyst utilized without adversely affecting the hydrosilation reaction. Thus, use of excess catalyst typically is avoided. The platinum concentration in the reaction medium typically ranges up to about 500 ppm by weight based on the weight of reactants and solvents. Preferably, the platinum concentration is up to about 250 ppm, more preferably between about 1 and 150 ppm, and most preferably between about 10 and 75 ppm.

Catalyst typically can be recovered from the desired product by distillation, and normally would be recovered in the distillation bottoms stream containing material heavier (i.e., less volatile) than the desired vinylalkoxysilane product. This heavy stream, which contains the bis-heavy material, typically is suitable as a solvent for the hydrosilation reaction. Therefore, catalyst conveniently can be recycled together with the heavy stream as a solvent. In the alternative, catalyst can be recovered separately from all reaction products for recycle or reclamation.

If desired, a small amount of a catalyst promoter can be used to enhance the performance of the platinum hydrosilation catalyst. The promoter facilitates transformation of the catalyst from a non-active or less active form to a more active form. Prior art has taught the use of triethylsilane or phenothiazine as hydrosilation catalyst promoters. See, for example, U.S. Pat. Nos. 3,925,434 and 4,614,812 which are incorporated herein by reference. Phenothiazine is a preferred catalytic promoter in the present invention.

Hydrosilation of an alkyne by an alkoxysilane in the presence of a platinum catalyst can yield a number of by-products, some of which are very difficult to separate from the desired product. As indicated above, it has been discovered that the concentration of certain contaminants, especially ionic chloride and alkyl amines, in the reaction medium significantly affects the selectivity of the hydrosilation reaction between an alkyne and an alkoxysilane and the formation of such undesired by-products. Typically, these contaminants are introduced into the reaction medium with the hydrosilation reactant, i.e., the alkoxysilane, because of its method of manufacture. In accordance with the method of this invention, the concentration of such contaminants in the reaction zone must be maintained at a low level, to produce a vinylalkoxysilane product of high purity and yield.

Although the inventors do not wish to be bound by any theory, it is believed that certain contaminants in the reaction medium, particularly ionic chloride and alkyl amines, form coordinate complexes with or react with the platinum hydrosilation catalyst. Such complexes make the catalyst less available for the desired reaction or change the nature of the catalyst to promote side reactions which decrease yield and contaminate the vinylalkoxysilane product.

Typically, the total concentration of alkyl amines (measured as nitrogen) and ionic chloride contaminants, individually and preferably in the aggregate, should not exceed about 0.10 weight percent, preferably their concentration should not exceed about 0.05 weight percent, in the reaction zone. More preferably, the total concentration does not exceed about 0.01 weight percent, and most preferably does not exceed about 0.005 weight percent. At these preferred contaminant levels in the reaction medium, the total concentration of tetraalkoxysilane and alkylalkoxysilanes by-products found in the desired product is not expected to exceed about 1 weight percent.

Alkoxysilanes suitable for use in the present invention typically can be made in accordance with the following reactions (some side reactions not shown):

A. Esterification of trichlorosilane $$HSiCl_3 + 3ROH \rightarrow HSi(OR)_3 + 3HCl$$

B. Esterification of tris(dimethylamino)silane $$HSi[N(CH_3)_2]_3 + 3ROH \rightarrow HSi(OR)_3 + 3HN(CH_3HN(CH_3)_2$$

C. Direct reaction of silicon and methanol $$Si + 3ROH \rightarrow HSi(OR)_3 + H_2$$

Esterification of trichlorosilane has been the most popular commercial method for making alkoxysilanes, even though the product contains chloride, both as soluble ionic chloride and in the form of a partial ester $HSi(OR)_2Cl$. Although very careful neutralization sometimes can be utilized to reduce the ionic chloride concentration to less than about 100 ppm (0.01 wt percent), removal of additional ionic chloride is difficult because the alkoxysilane reacts with the added alkaline materials. Removal of alkyl amines from the trialkoxysilane produced by esterification of tris(dimethylamino)silane also is very difficult.

Many commercial sources of alkoxysilanes likely will have been prepared by one of these two procedures. Consequently, purification of the alkoxysilane, such as by distillation, may be necessary to reduce its level of chloride and alkyl amine contamination before it is used in the present invention. Since the direct reaction of silicon and methanol produces no chloride or alkyl amine in the desired alkoxysilane product, the third source of alkoxysilane is preferred for preparing vinylalkoxysilanes used according to the present invention. A direct process for preparing alkoxysilanes is described, for example, in Mendicino U.S. Pat. No. 4,727,173 which is incorporated herein by reference.

Although not always required, it often is convenient, particularly where batch-type operation is desired, to carry out the reaction in the presence of a solvent, especially if chloroplatinic acid is utilized as the catalyst. Suitable solvents preferably have a high solubility for the reactants. Exemplary solvents include o-dichlorobenzene, by-product bis(alkoxysily)alkane and the vinylalkoxysilane product itself. In a particularly useful embodiment, the product vinylalkoxysilane can constitute essentially the sole solvent. It is particularly surprising that the product can be used as a reaction solvent without disastrous results on purity and yield since its reaction with the alkoxysilane is a primary source of bis(alkoxysilyl)alkane, i.e., bis-heavy, formation. Other organic solvents, for example cumene, toluene or xylene, also are suitable. The method of the present invention provides a relatively low cost, safe method for efficiently producing the desired vinylalkoxysilane product in high yield and high purity.

The conditions of pressure and temperature at which the hydrosilation reaction is carried out in accordance with the method of the present invention are selected to minimize formation of unwanted by-products. While the temperature must be high enough to ensure acceptable catalyst activity and selectivity, too high or too low a temperature may favor the formation of the unwanted tetraalkoxysilane and hydrogenated vinylsilane by-products. The choice of catalyst, the particular reactants and the desired operating pressure, to some extent, influence the temperature chosen. Optimum conditions can be selected using routine experimentation. To maintain acceptable activity with chloroplatinic acid catalyst, for example, the reaction temperature normally should be at least about 50° C. Although in some cases the reaction proceeds well at temperatures of 150° C. and higher, generally a reaction temperature above about 150° C., is not preferred; as this tends to increase the formation of tetraalkoxysilane and alkylalkoxysilanes, typically to levels beyond that acceptable (i.e. greater than about 1 weight percent). See, for example, U.S. Pat. No. 4,579,965. Thus, the temperature at which the reaction is carried out in accordance with the method of the present invention preferably is within the range of about 50° to 150° C., more preferably between about 85° and 150° C. and most preferably between about 100° and 150° C.

While higher reaction pressures (up to about 20 atmosphere pressure) favor improved product selectivity, one of the advantages of the method of the present invention is that lower acetylene pressure are acceptable. Thus, even at an acetylene (i.e., alkyne) pressure of about 75 psi absolute, and especially at a pressure of 25-30 psi absolute and below, i.e., at atmospheric pressure up to about 15 pounds per square inch gauge pressure, product yield and selectivity remain satisfactory in the process of the present invention, with the undesired hard to separate by-products in the product being produced in an amount of less than about 1 weight percent at preferred reaction conditions. By maintaining desired reactant purities and adequately controlling temperature, undesired reactions, including the formation of bis-heavy product, are avoided without necessitating high acetylene pressure. Thus, the method of the present invention provides a safe process for making vinylalkoxysilanes.

A variety of reactors can be used for the hydrosilation reaction and the present invention is not limited to any particular reactor type or design. Suitable reactors include an addition reactor with continuous feed, a continuous stirred tank reactor (CSTR), and a packed column reactor. A preferred reactor generally would be one which selectively removes product (vinylalkoxysilane), but not raw material (alkyne and alkoxysilane), such as a countercurrent column reactor or a distillative reactor. In such reactors, the product is continuously removed from the bottom, at which point the acetylene is fed; the alkoxysilane preferably is fed at the other end of the column to minimize contact between product and alkoxysilane reactant. Alternatively, a bubbling column reactor may be used, in which case the product is removed overhead.

The present invention will be described in greater detail with reference to the following examples, in which the parts and percentages are by weight unless otherwise indicated.

EXAMPLES 1-5

A 500 ml three-neck flask as the reaction zone was equipped with a trimethoxysilane (TMS) charge funnel, a dry ice condenser, a thermometer, an acetylene sparger, and a magnetic stirring bar. The flask was initially charged with 250 to 300 grams of o-dichlorobenzene (o-DCB) as the reaction solvent, 330 microliters chloroplatinic acid (CPA) solution (10% CPA in ether-alcohol) as the hydrosilation catalyst and 0.05 grams phenothiazine (PZ) as a catalytic promoter. The reaction medium so-formed contained 50 ppm Pt as CPA and 200 ppm PZ. The reactor was thoroughly purged by acetylene and the contents were heated to 100° C.

Acetylene was fed into the reaction zone at a rate of 0.36 mole/hr through the sparger below the liquid surface and high purity trimethoxysilane was fed at a rate of 0.22 mole/hr. The reaction zone was maintained at atmospheric pressure. After about two hours feeding of trimethoxysilane and acetylene into the reaction zone, trimethoxysilane feed was stopped and the reactor was cooled for sampling. This procedure was repeated four additional times. The chemical analysis of a sample from each of the five runs is shown in Table 1. The measure concentrations are normalized to remove the weight fraction of solvent.

The 5 runs averaged 92.2 percent vinyltrialkoxysilane, 6.2 percent bis(trimethoxysily)ethane(Bis-Hvs), 0.12 percent tetramethoxysilane ($Si(OMe)_4$), and 0.06 percent ethyltrimethoxysilane (EtTMS). Thus, the total concentration of tetraalkoxysilane and alkylalkoxysilanes in the product was less than 1.0 wt. percent.

TABLE 1

| Ex. | Normalized Undistilled Product (wt pct) | | | | Product yield |
|---|---|---|---|---|---|
| | $Si(OMe)_4$ | Product | EtTMS | Bis-Hvs | % mole |
| 1 | 0.358 | 92.763 | 0.000 | 4.999 | 88.543 |
| 2 | 0.000 | 92.944 | 0.000 | 6.001 | 87.206 |
| 3 | 0.000 | 95.016 | 0.000 | 3.888 | 90.548 |
| 4 | 0.090 | 92.206 | 0.041 | 6.390 | 91.341 |
| 5 | 0.157 | 87.938 | 0.247 | 9.876 | 86.879 |
| Avg. | 0.121 | 92.173 | 0.058 | 6.231 | 88.903 |

EXAMPLES 6-11

The reaction between acetylene and trimethoxysilane was carried out in accordance with the procedure and conditions of Examples 1-5 except that different catalysts were substituted for the CPA hydrosilation catalyst and PZ catalytic promoter combination. The results of these tests are summarized in Table 2.

TABLE 2

| Ex. No | Catalyst | Normalized Undistilled Product (wt. percent) | | | | Product Yield |
|---|---|---|---|---|---|---|
| | | $Si(OMe)_4$ | Product | EtTMS | Bis-Hvs | % mole |
| 1-5* | CPA/PZ | 0.121 | 92.173 | 0.058 | 6.231 | 88.903 |
| 6 | Pt(AcAc)$_2$ | 0.330 | 88.437 | 0.451 | 10.222 | 79.980 |

TABLE 2-continued

| Ex. No | Catalyst | Normalized Undistilled Product (wt. percent) | | | | Product Yield % mole |
|---|---|---|---|---|---|---|
| | | Si(OMe)$_4$ | Product | EtTMS | Bis-Hvs | |
| 7 | Pt(AcAc)$_2$Cl$_2$ | 0.532 | 50.054 | 2.401 | 26.170 | 39.028 |
| 8 | Pt(PPh$_3$)$_2$Cl$_2$ | 0.117 | 87.284 | 0.000 | 1.905 | 73.160 |
| 9 | CPA/Silica | 0.07 | 82.434 | 0.342 | 14.073 | 80.148 |
| 10 | CPA | 0.063 | 88.230 | 0.261 | 9.424 | 86.870 |
| 11 | Recycle-CPA/PZ | nd | 82.993 | 0.278 | 14.608 | 78.747 |

*Average values from Table 1.
nd = none detected

EXAMPLES 12-13

The reaction between acetylene and trimethoxysilane was carried out in accordance with the procedure and conditions of Examples 1-5, except that the catalyst concentration was reduced to 25 and 12 ppm Pt respectively. The results are reported in Table 3.

TABLE 3

| Ex. No | Platinum by CPA ppm | Temp. °C. | Normalized Undistilled Product (wt. percent) | | | | Product yield % mole |
|---|---|---|---|---|---|---|---|
| | | | Si(OMe)$_4$ | Product | EtTMS | Bis-Hvs | |
| 12 | 12 | 100 | 0.984 | 81.851 | 0.258 | 11.100 | 76.531 |
| 13 | 25 | 100 | 0.367 | 87.624 | 0.260 | 9.531 | 83.638 |
| 1-5* | 50 | 100 | 0.121 | 92.173 | 0.058 | 6.231 | 88.903 |

*Average values from Table 1.

EXAMPLES 14-16

The reaction between acetylene and trimethoxysilane was carried out in accordance with the procedures of Examples 1-5, except that the reaction temperature was altered. The results are reported in Table 4.

TABLE 4

| Ex. No | Platinum by CPA ppm | Temp. °C. | Normalized Undistilled Product (wt. percent) | | | | Product yield % mole |
|---|---|---|---|---|---|---|---|
| | | | Si(OMe)$_4$ | Product | EtTMS | Bis-Hvs | |
| 14 | 50 | 85 | 1.259 | 80.474 | 0.250 | 10.324 | 75.074 |
| 15 | 50 | 130 | 0.397 | 90.503 | 0.205 | 7.131 | 85.755 |
| 16 | 50 | 150 | 0.063 | 88.230 | 0.261 | 9.424 | 86.870 |
| 1-5* | 50 | 100 | 0.121 | 92.173 | 0.058 | 6.231 | 88.903 |

*Average values from Table 1.

EXAMPLE 17

The reaction between acetylene and trimethoxysilane was carried out in accordance with the procedures and conditions of Examples 1-5, except that bis(trimethoxysilane)ethane was used as the reaction solvent in place of o-DCB. Based on an analysis of the final reaction medium the yield of the desired vinyltrialkoxysilane product was about 89% and contained less than 1% of the combination of tetramethoxysilane and ethyltrimethoxysilane.

EXAMPLES 18-19

Examples 18 and 19 were conducted in a 1-liter glass pressure reactor as the reaction zone, equipped with a stirrer, heating jacket, and a temperature controller. The reactor was initially charged with 250 grams o-dichlorobenzene (o-DCB) as the reaction solvent, 300 microliters of chloroplatinic acid solution (10 percent chloroplatinic acid in ether and ethanol solution) as the hydrosilation catalyst, and the reaction zone was purged with acetylene. The reaction medium was heated to 100° C. and maintained at that temperature and the reactor was pressurized to 21.7 psia. High purity trimethoxysilane (TMS) was fed into the reaction zone at a rate of 0.98 mole/hr; acetylene was introduced on demand at a rate sufficient to maintain a reaction zone pressure of 21.7 psia (no excess acetylene was required). After feeding 0.5 mole of TMS, a sample of unfractionated reaction product was taken for analysis. In Example 19 the o-DCB reaction solvent was replaced with vinyltrimethoxysilane (VTMS), i.e., the product was utilized as solvent. The results are reported in Table 5.

TABLE 5

| Ex. No | Acetylene Press. Psia | Normalized Undistilled Product (wt. percent) | | | | Product yield % mole | Reaction Solvent |
|---|---|---|---|---|---|---|---|
| | | Si(OMe)$_4$ | Product | EtTMS | Bis-Hvs | | |
| 1-5* | 14.7 | 0.121 | 92.173 | 0.058 | 6.231 | 88.903 | O-DCB |
| 18 | 21.7 | nd | 95.946 | nd | 3.314 | 94.651 | O-DCB |
| 19 | 21.7 | 0.376 | 87.490 | 0.061 | 7.468 | 86.355 | VTMS |

*Average values from Table 1.

EXAMPLES 20-23

The reaction between trimethoxysilane (TMS) and acetylene was carried out in accordance with the procedures and conditions of Examples 18 and 19, except for variations in reactor pressure, adjustments of the TMS feed rate, or the addition of PZ promoter. The results, as compared with the average value for Examples 1–5 and the results of Example 18 are listed in Table 6.

TABLE 6

| Ex. No | Actyln Press Psia | TMS Feed mol/hr | PZ Promoter ppm | Normalized Undistilled Product (wt. percent) | | | | Product yield % mole |
|---|---|---|---|---|---|---|---|---|
| | | | | Si(OMe)$_4$ | Product | EtTMS | Bis-Hvs | |
| 1–5* | 14.7 | 0.22 | 200 | 0.121 | 92.173 | 0.058 | 6.231 | 88.903 |
| 18 | 21.7 | 0.98 | 0 | nd | 95.946 | nd | 3.314 | 94.651 |
| 20 | 23.7 | 0.22 | 200 | 0.093 | 97.127 | trace | 1.962 | >95.0 |
| 21 | 23.7 | 0.22 | 0 | nd | 96.400 | nd | 3.170 | 91.200 |
| 22 | 22.2 | 0.49 | 0 | nd | 97.100 | nd | 2.430 | 94.400 |
| 23 | 27.4 | 1.96 | 0 | nd | 95.555 | 0.143 | 3.737 | 94.350 |

*Average values from Table 1.

EXAMPLES 24–26

The reaction between trimethoxysilane and acetylene was run in the equipment and in accordance with the procedures and conditions of Examples 1–5, except that dimethylamine (DMA) or trichlorosilane containing ionic chloride impurity (Cl) was added to the high purity trimethoxysilane to provide known contaminants in a known concentration. In both cases, the reactions ran poorly with both low product yield and low purity. As summarized in Table 7, the concentrations of bis(trimethoxysilane)ethane, ethyltrimethoxysilane, and tetramethoxysilane were higher in the product sample. In addition, trimethoxysilane was not completely reacted for the runs with 0.3 percent dimethylamine and 0.1 percent chloride in trimethoxysilane.

TABLE 7

| Ex. No | Impurity Added in TMS | Residual HSi(OMe)$_3$ | Normalized Undistilled Product, wt. percent | | | | Product yield % mole |
|---|---|---|---|---|---|---|---|
| | | | Si(OMe)$_4$ | Product | EtTMS | Bis-Hvs | |
| 1–5* | None | ND | 0.121 | 92.173 | 0.058 | 6.231 | 88.903 |
| 24 | 0.3% DMA | 9.548 | 2.993 | 42.790 | 4.751 | 36.630 | 32.630 |
| 25 | 0.1% Cl | 0.328 | 0.974 | 48.779 | 1.899 | 32.813 | 49.470 |
| 26 | 0.01% Cl | ND | 0.307 | 73.942 | 0.626 | 21.249 | 72.069 |

*Average values from Table 1.

EXAMPLE 27

Using apparatus similar to that employed in the prior examples, trimethoxysilane (TMS) was used to hydrosilate acetylene at a temperature of 120° C. and a pressure of 27.7 psia. o-DCB was used as a reaction solvent and chloroplatinic acid yielding a concentration of 10 ppm platinum as catalyst. The reactor was initially charged with acetylene before starting TMS feeding. While the acetylene was introduced at substantially a constant rate of 0.5 mole/hr into the reaction zone, TMS was pulse fed using a ten minute cycle with feeding at a rate of about 5 g-moles/hr. for the first minute and no feed for the remaining 9 minutes of the cycle. Product was sampled every hour. Performance results are summarized in Table 8 below.

TABLE 8

| Sample No. | Normalized Undistilled Product (wt. percent) | | |
|---|---|---|---|
| | Product | Bis-Hvs | Hard-to-Separate By-Products |
| 1 | 76.7 | 21.8 | 0.87 |
| 2 | 71.5 | 27.2 | 0.91 |
| 3 | 67.7 | 31.0 | 0.94 |
| 4 | 65.3 | 33.5 | 0.93 |
| 5 | 65.8 | 32.9 | 1.05 |

EXAMPLES 28–30

Using apparatus and conditions similar to those of Example 18, trimethoxysilane (TMS) was used to hydrosilate acetylene respectively at temperatures of 65° C., 47° C. and 25° C. and at a pressure of 27 psia. O-dichlorobenzene was used as the reaction solvent (diluent) and sufficient chloroplatinic acid yielding a platinum concentration of 50 ppm as a catalyst. In each case, the reaction medium also contained 200 ppm phenothiazine as a catalyst promoter. A sample of the reaction medium, normalized and undistilled, contained for the 65° C. reaction: 87.3% vinyltrimethoxysilane product, 10.4% bis-heavies and 1.3% hard-to-separate impurities; for the 47° C. reaction: 92.1% vinyltrimethoxysilane product, 5.5% bis-heavies and 1.2% hard-to-separate impurities; and for the 25° C. reaction: 35.8% vinyltrimethoxysilane product, 15.8% bis-heavies and 3.1% hard-to-separate impurities.

EXAMPLE 31

Using apparatus and conditions similar to those of Example 18, methyldimethoxysilane was used to hydrosilate acetylene at a temperature of 120° C. and a pressure of 27 psia. o-Dichlorobenzene was used as the reaction solvent (diluent) and sufficient chloroplatinic acid to yield a platinum concentration of 50 ppm as a catalyst. The reaction medium also contained 200 ppm phenothiazine as a catalyst promoter. A sample of the reaction medium, normalized and undistilled, contained 96.0% methylvinyldimethoxysilane product, 2.5% bis-heavies and 0.14% hard-to-separate impurities.

While certain specific embodiments of the present invention have been described with particularity herein, it will be recognized that various modifications thereof will occur to those skilled in the art and it is to be understood that such modifications and variations are to be included within the purview of this application and the spirit and scope of the appended claims. Throughout the specification, the method of the invention has been described particularly with respect to acetylene and a trialkoxysilane as the reactants. However, references to specific compounds, and in particular to acetylene and to specific trialkoxysilanes, such as trimethoxysilane and triethoxysilane, should not be considered to limit

We claim:

1. A process for producing a vinylalkoxysilane which comprises
   (i) gradually feeding to a reaction zone an alkoxysilane of the formula $HSi(OR')_nR''_{3-n}$ where R' and R'' can individually be the same or different and are selected from primary alkyl groups of 1 to 6 carbon atoms and n is 1, 2 or 3, said reaction zone containing an alkyne of the formula $RC\equiv CH$ where R is hydrogen or a monovalent hydrocarbon radical of 1 to 10 carbon atoms and a platinum hydrosilation catalyst;
   (ii) contacting said alkyne and said alkoxysilane in said reaction zone in the presence of said platinum hydrosilation catalyst and less than 0.1 weight percent ionic chloride and alkyl amine to form vinylalkoxysilane; and
   (iii) recovering said vinylalkoxysilane from said reaction zone.

2. A process for producing a vinylalkoxysilane which comprises
   (i) co-feeding to a reaction zone an alkyne of the formula $RC\equiv CH$ where R is hydrogen or a monovalent hydrocarbon radical of 1 to 10 carbon atoms and an alkoxysilane of the formula $HSi(OR')_nR''_{3-n}$ where R' and R'' can individually be the same or different and are selected from primary alkyl groups of 1 to 6 carbon atoms and n is 1, 2 or 3;
   (ii) contacting said alkyne and said alkoxysilane in said reaction zone in the presence of a platinum hydrosilation catalyst and less than 0.1 weight percent ionic chloride and alkyl amine to form vinylalkoxysilane; and
   (iii) recovering a product stream containing said vinylalkoxysilane from said reaction zone.

3. The process of claim 2 wherein said alkyne is acetylene.

4. The process of claim 1, 2 or 3 wherein R' and R'' are selected from primary alkyl groups of 1 to 4 carbon atoms.

5. The process of claim 1, 2 or 3 wherein said alkoxysilane is selected from the group consisting of trimethoxysilane, triethoxysilane, tris(methoxyethoxy)silane, tributoxysilane, methyldimethoxysilane, dimethylmethoxysilane, methyldiethoxysilane, tripropoxysilane, tripentoxysilane, and tris(2-ethylhexoxy)silane.

6. The process of claim 1, 2 or 3 wherein said alkoxysilane is selected from trimethoxysilane and triethoxysilane.

7. The process of claim 1, 2 or 3 where said platinum hydrosilation catalyst is chloroplatinic acid.

8. The process of claim 1, 2 or 3 where said reaction zone is at a pressure of less than 75 psia.

9. The process of claim 8 wherein said pressure is less than 25 psia.

10. The process of claim 1, 2 or 3 wherein said reaction zone has a temperature between about 50° and about 150° C.

11. The process of claim 10 wherein said temperature is between about 85° and about 150° C.

12. The process of claim 1, 2 or 3 wherein said alkoxysilane is produced by direct reaction between silicon and methanol.

13. The process of claim 1, 2 or 3 wherein said contacting is done in the presence of a solvent selected from the group consisting of cumene, toluene, xylene, o-dichlorobenzene, vinylalkoxysilane, bis(alkoxysilyl)alkane and mixtures thereof.

14. The process of claim 7 wherein said reaction zone contains phenothiazine.

15. A continuous process for producing a vinylalkoxysilane which comprises
   (i) co-feeding into a reaction zone an alkyne and an alkoxysilane wherein said alkyne is fed into said reaction zone at a rate which keeps the molar ratio of said alkyne to said alkoxysilane in said reaction zone between about 1.0 to 10.0, said alkyne having a formula $RC\equiv CH$ where R is hydrogen or a monovalent hydrocarbon radical of 1 to 10 carbon atoms and said alkoxysilane having a formula $HSi(OR')_nR''_{3-n}$ where R' and R'' can individually be the same or different and are selected from primary alkyl groups of 1 to 6 carbon atoms and n is 1, 2 or 3,
   (ii) contacting said alkyne and said alkoxysilane in said reaction zone in the presence of a platinum hydrosilation catalyst and less than 0.1 weight percent ionic chloride and alkyl amine to form vinylalkoxysilane; and
   (iii) simultaneously removing a product stream containing said vinylalkoxysilane from said reaction zone.

16. The process of claim 15 wherein said alkyne is acetylene.

17. The process of claim 16 wherein said alkoxysilane is selected from trimethoxysilane and triethoxysilane.

18. The process of claim 17 where said platinum hydrosilation catalyst is chloroplatinic acid.

19. The process of claim 18 where said reaction zone is at an acetylene pressure of less than about 75 psia.

20. The process of claim 15 wherein said reaction zone has a temperature between about 50° and about 150° C.

21. The process of claim 16 or 17 wherein said alkoxysilane is produced by direct reaction between silicon and methanol.

22. The process of claim 15 wherein the feed rate of said alkyne keeps the molar ratio in said reaction zone between 1.0 and 5.0.

23. The process of claim 18 wherein said reaction zone contains phenothiazine.

24. The process of claim 16 or 19 wherein said acetylene is feed into said reaction zone at a rate needed to maintain a substantially constant pressure in said reaction zone.

* * * * *